United States Patent [19]

Zupancic et al.

[11] Patent Number: 5,012,505

[45] Date of Patent: Apr. 30, 1991

[54] FLUIDIC SLIP RING FOR CT SCANNERS

[75] Inventors: Anton Z. Zupancic, Kirtland; Anthony Palermo, Chesterland; Robert E. Levar, Willoughby, all of Ohio

[73] Assignee: Picker International, Inc., Highland Hts., Ohio

[21] Appl. No.: 354,384

[22] Filed: May 19, 1989

[51] Int. Cl.$^5$ .............................. A61B 6/03; H01J 1/42
[52] U.S. Cl. .................... 378/130; 378/200; 378/15; 378/199
[58] Field of Search ............... 378/33, 4, 15, 11, 126, 378/21, 141, 130, 199, 201, 202, 203, 127, 200

[56] References Cited

U.S. PATENT DOCUMENTS

| | | | |
|---|---|---|---|
| 4,644,573 | 2/1987 | Palermo et al. | 378/15 |
| 4,651,338 | 3/1987 | Hahn | 378/199 |
| 4,709,559 | 12/1987 | Dotzauer et al. | 378/200 |
| 4,853,946 | 8/1989 | Elliot et al. | 378/4 |
| 4,866,743 | 9/1989 | Kroener | |

Primary Examiner—Janice A. Howell
Assistant Examiner—Don Wong
Attorney, Agent, or Firm—Fay, Sharpe, Beall, Fagan, Minnich & McKee

[57] ABSTRACT

A patient receiving region (12) is defined within a stationary CT scanner frame (A). An x-ray tube (B) is mounted on a rotating frame portion (40) for rotation about the patient receiving region on an annular bearing (44, 46, 48). A fluidic slip ring (60) is mounted between the rotating and stationary frames adjacent the bearing for conveying cooling fluid between the x-ray tube and a stationarily mounted, preferably off-site, chiller (D). The fluidic slip ring enables large amounts of heat to be removed from the x-ray tube to maintain the x-ray tube at proper operating temperatures without overheating the interior of the CT scanner, the CT scanner room, or the like.

18 Claims, 5 Drawing Sheets

FLUIDIC SLIP RING FOR CT SCANNERS

BACKGROUND OF THE INVENTION

The present invention relates to the radiography art. It finds particular application in conjunction with computerized tomographic (CT) scanners and will be described with particular reference thereto. However, it is to be appreciated that the present invention may also find application in conjunction with other radiation treatment apparatus and imaging apparatus.

Heretofore, tomographic scanners have commonly included a floor-mounted frame assembly which remains stationary during a scan. An x-ray tube is mounted to a rotatable frame assembly which rotates around a patient receiving examination region during the scan. Radiation from the x-ray tube traverses the patient receiving region and impinges upon an array of radiation detectors. From the radiation data sampled by the detectors and the position of the x-ray tube during each sampling, a tomographic image of one or more slices through the patient is reconstructed.

An x-ray tube generates x-rays by directing a high energy electron beam against a tungsten target. One of the persistent problems in CT scanners and other radiographic apparatus is dissipating the waste heat created while generating x-rays. In higher powered x-ray tubes, the anode turns so that the high energy electron beam only dwells a fraction of a second at a time on any point on the anode. The x-ray tube is jacketed with a lead lined housing. A cooling oil is circulated between the glass envelope of the x-ray tube and the housing to remove additional heat.

In some scanners, the x-ray tube rotates in one direction during a scan and returns in the other direction for the next scan. Such scanners are normally limited to about 360° of rotation. The single rotation enables the hot cooling oil to be conveyed from the rotating frame by flexible hoses to a non-rotating heat exchanger. Accommodating the cooling oil-carrying hoses is a space consumptive handling problem. The heat exchanger is commonly a radiator disposed within the CT scanner housing that is cooled by fans which blow room air through the heat exchanger and back into the room. This places an extra load on the room air conditioning system.

In other CT scanners, the cooling oil is circulated to a radiator or other air-oil heat exchanger that is mounted on the rotating frame portion. This alleviates the hose handling problems and enables the x-ray tube to rotate a plurality of times, e.g. a continuous rotate scanner. However, accommodating the size and weight of the heat exchanger in the tight space constraints of the rotating frame is difficult. As the x-ray tube and rotating frame portion rotate, air passes through the heat exchanger cooling the oil. The heated air that is discharged into the room that contains the CT scanner again places a greater load on the room air conditioning system.

One of the limiting factors on the speed of a CT scan is the amount of x-rays produced by the x-ray tube. The tube must irradiate each detector for a sufficient duration that each detector receives the minimum total flux needed to reconstruct a good contrast image. Lower power tubes require the tube to dwell or focus longer on each detector. Larger, more powerful x-ray tubes supply the minimum flux more quickly, allowing the speed of rotation to be increased, hence the scan time decreased. However, as the x-ray tubes become more powerful, more heat is generated. More heat is also generated in continuous rotate scanners in which the tube remains "on" during several consecutive rotations for multislice imaging.

Larger x-ray tubes, such as seven inch anode x-ray tubes, generate so much heat that the prior art heat dissipation techniques are taxed. The limited air volume in the interior of a CT scanner limits the effectiveness of the rotating oil-air heat exchanger. Space constraints prevent larger heat exchangers from being accommodated on the rotating frame. Moreover, the added heat taxes the cooling capacity of room air conditioning systems to the point that room cooling capacity must be increased.

The present invention provides a new and improved cooling system which overcomes the above referenced problems and others.

SUMMARY OF THE INVENTION

In accordance with one aspect of the present invention, a radiographic apparatus is provided. A fluid slip ring provides fluid communication between a fluid cooling means and a rotatable x-ray tube carrying frame and, preferably, the x-ray tube carried thereon. A fluid circulating means circulates cooling fluid through the slip ring between the cooling means and the rotatable frame.

In accordance with a yet more limited aspect of the present invention, the x-ray tube is mounted on a rotatable frame that is continuously rotatable. An array of x-ray detectors are stationarily mounted to receive radiation from the x-ray tube that has traversed a patient examination region. An image reconstruction means reconstructs an image representation from data received by the radiation detector array.

In accordance with another aspect of the present invention, the fluidic slip ring includes first and second mating annular portions, the first annular portion has a smooth surface facing the second annular portion, and the second annular portion has a plurality of open channels facing the smooth surface. One channel receives cool incoming cooling fluid to cool the x-ray tube and another channel receives cooling fluid heated by the x-ray tube. Seals are disposed adjacent these channels.

In accordance with a yet more limited aspect of the present invention, the cooling fluid carrying channels are adjacent the center of the fluidic slip ring. A pair of leakage receiving channels are defined on either side of the cooling fluid carrying channels for collecting fluid that is passed across the intervening seals.

One advantage of the present invention is that it effectively cools x-ray tubes.

Another advantage of the present invention is that it enables heat from the x-ray tube to be dissipated externally of the scanner and control rooms. Bigger, higher capacity heat exchangers are readily accommodated.

Another advantage of the present invention is that it facilitates the use of higher power x-ray tubes.

Another advantage of the present invention is that it enables the x-ray tube and rotating frame to rotate continuously.

Still further advantages of the present invention will become apparent to those of ordinary skill in the art upon reading and understanding the following detailed description of the preferred embodiment.

BRIEF DESCRIPTION OF THE DRAWINGS

The invention may take form in various parts and arrangements of parts or in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
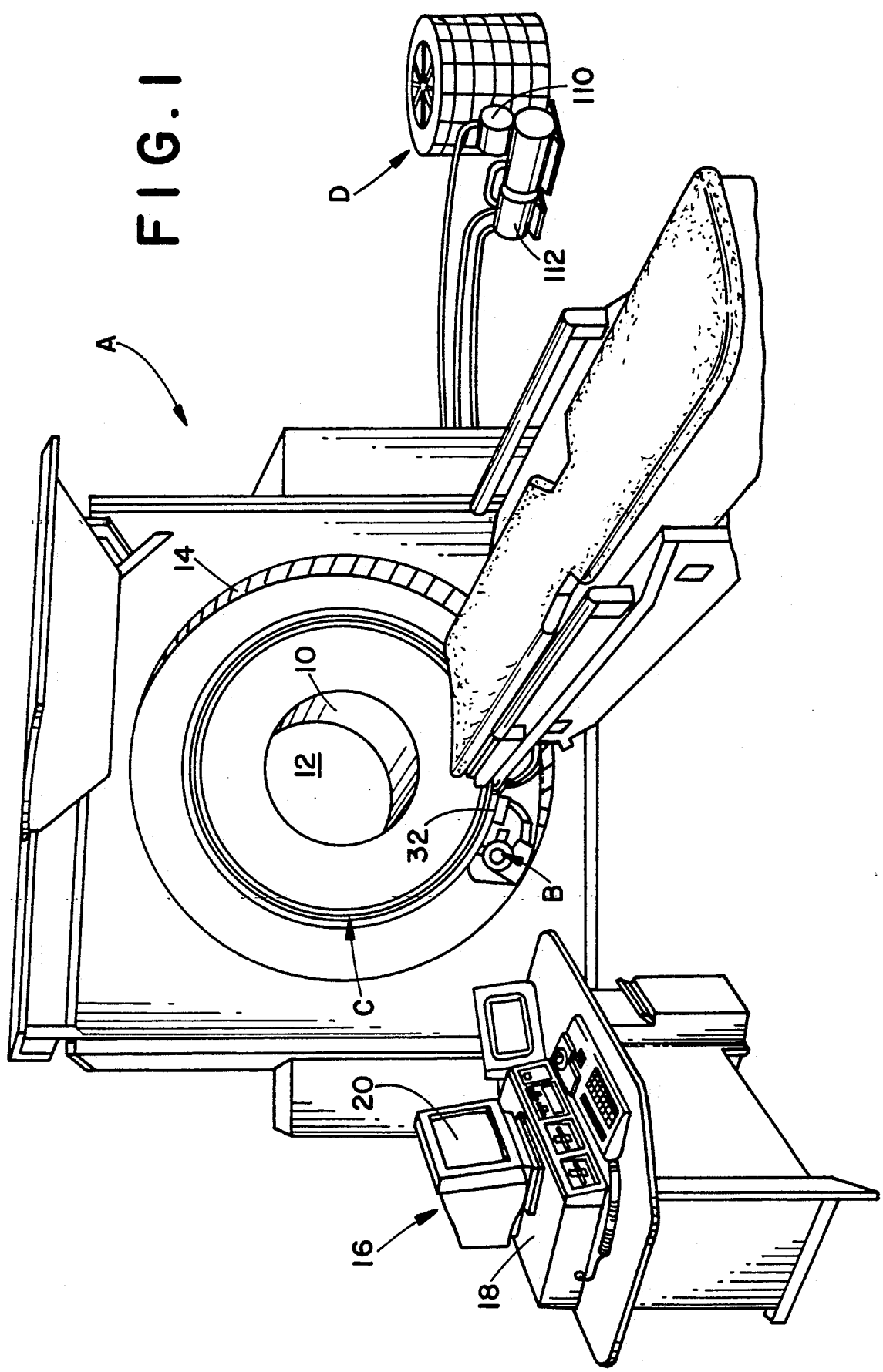
FIG. 1 is a diagrammatic illustration of a CT scanner in accordance with the present invention.

With reference to FIG. 1, a CT scanner includes a floor-mounted or stationary frame portion A whose position remains fixed during data collection. An x-ray tube B is rotatably mounted by a bearing and fluidic slip ring assembly C for continuous rotation. The fluidic slip ring passes a cooling fluid, such as oil, water, sulfur, hexafluoride, and other liquids and gases, between an externally mounted chilling unit or heat exchanger D and the rotatably mounted x-ray tube B.

The stationary frame portion A includes a cylinder 10 that defines a patient receiving examination region 12 therein. An array of radiation detectors 14 are disposed concentrically around the patient receiving region. The stationary frame with the rotating frame can be canted or tipped to scan slices at selectable angles. A control console 16 contains an image reconstructing means 18 for reconstructing an image representation of output signals from the detector array 14. A video monitor 20 converts the reconstructed image representation into a man-readable display. The console also includes appropriate tape and disk recording means for archiving image representations, performing image enhancements, and the like. Various control functions, such as initiating a scan, selecting among different types of scans, calibrating the system, and the like are also performed at the control panel.

Figure 2:
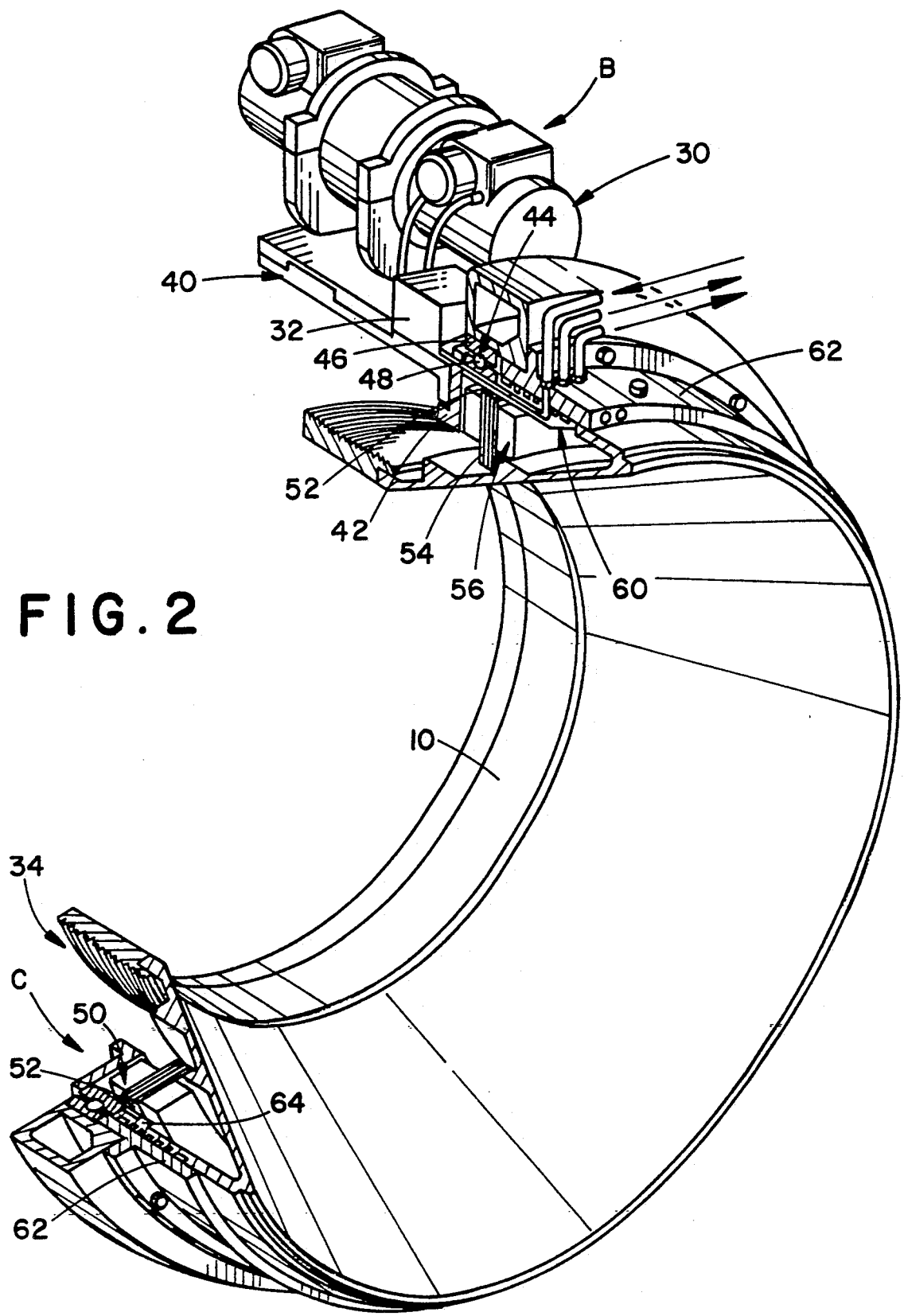
FIG. 2 is a perspective view in partial section of the fluidic slip ring of FIG. 1 and associated hardware including a drive motor for rotating the x-ray tube supporting rotating frame.

With continuing reference to FIG. 1 and further reference to FIG. 2, the x-ray tube B is enclosed in an oil-filled housing 30 that has an x-ray permeable window directed toward the patient receiving region 12. Inside the housing, a motor rotates an anode, such as a seven inch anode, in the plane of the patient receiving region and the x-ray transmissive window. An oil pump circulates the oil from the housing through a heat exchanger 32. The heat exchanger transfers heat from the oil to a liquid coolant.

An electron beam emitted by a cathode strikes the rotating anode adjacent the window such that x-rays are emitted through the window. Appropriate x-ray collimators focus the radiation into one or more planar beams, or the like, as are conventional in the art. A shutter under control from the console selectively gates the beam on and off to control patient dosage. Electrical power from the console is conveyed to an electrical slip ring 34 that is mounted in association with the bearing and fluidic slip ring assembly C. A high voltage power supply is mounted for rotation in association with the x-ray tube for converting the lower voltage conveyed across the electrical slip ring to the appropriate high voltages for operating the x-ray tube.

With particular reference to FIG. 2, the x-ray tube B is mounted on a rotating x-ray tube support or frame 40. The rotating frame assembly includes an annular ring portion 42 which is connected with a rotating race 44 of a large bearing that surrounds the patient receiving region. The bearing also includes a stationary race 46 that is mounted to an annular tubular structure of the stationary frame assembly A. The bearing also includes a plurality of balls or rollers 48 for providing smooth rolling interaction between the rotating and stationary races. A motor 50 rotates the x-ray tube and rotatable frame relative to the stationary frame. The motor includes a plurality of permanent magnets 52 that are mounted on a lower surface of the rotating race 44 for rotation therewith. An annular motor lamination 54 and surrounding windings 56 create electrical fields which drive the magnets 52 and are mounted to the patient receiving tube 10 which is also mounted to the stationary frame assembly. Interaction of the winding and permanent magnetic fields rotates the rotatable frame assembly relative to the stationary frame.

Figure 3:
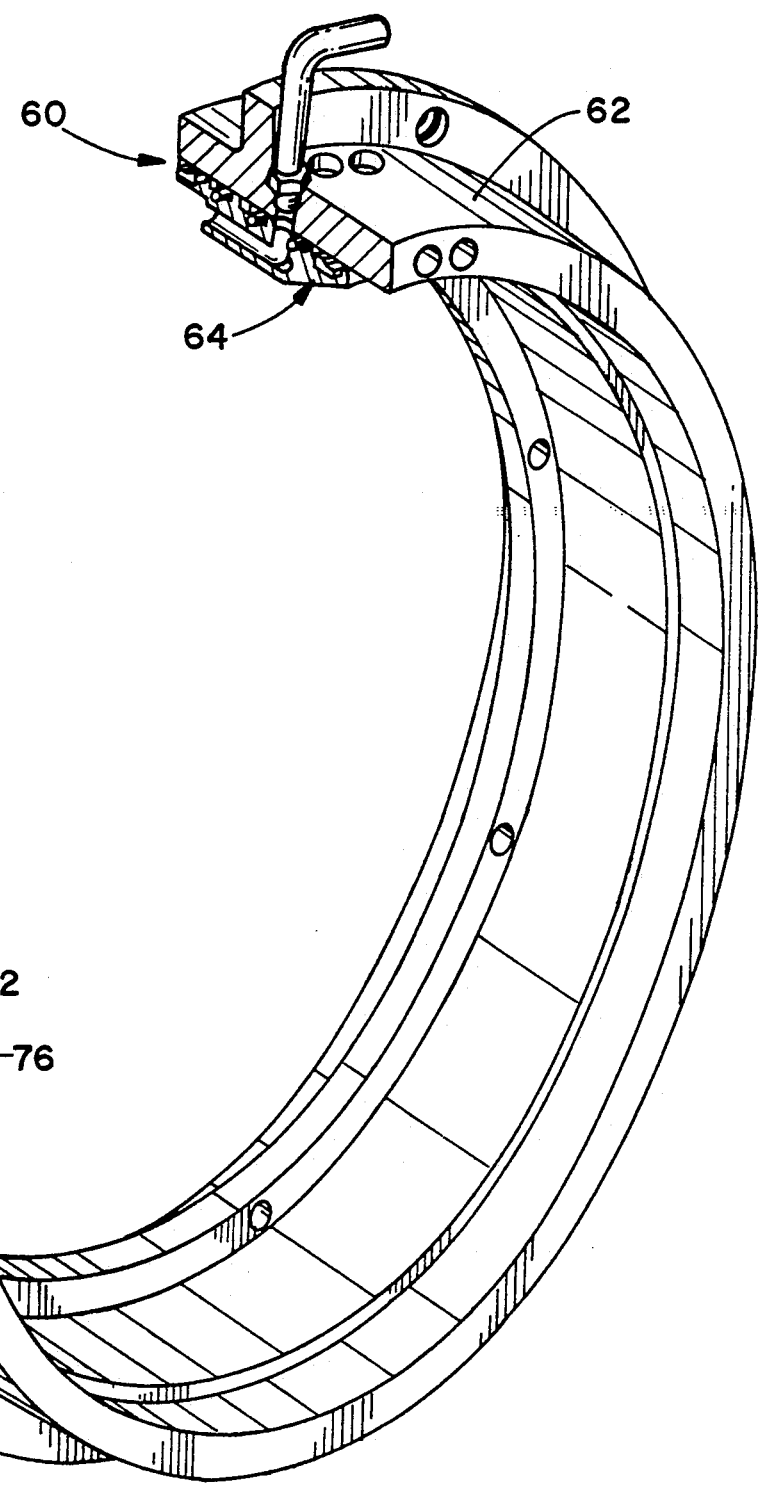
FIG. 3 is a more detailed illustration of the fluidic slip ring in partial section.

With reference to FIG. 3, a fluidic slip ring 60 is connected with the stationary and rotating frame portions. The fluidic slip ring includes an outer, stationary annular portion 62 that is mounted to the annular tubular structure and the patient receiving sleeve 10. In the illustrated embodiment, the stationary annular portion has a smooth, flat inner surface. The fluidic slip ring also includes a rotatable annular portion 64 which is connected with the rotating bearing race 44 and the rotating frame portion 40. The rotating annular portion 64 includes a plurality of channels or grooves, including an incoming cooling fluid channel 66 and an outgoing cooling fluid channel 68. A series of seal receiving grooves or channels 70 are disposed between and to either side of the fluid carrying channels 66, 68. Gaskets or seals 72 are carried in each groove to isolate the incoming and outgoing cooling fluid and to prevent leakage. A pair of leakage channels 74 are disposed outward from the outermost seals to retrieve any fluid that might leak past the fluid seals. A pair of final leakage seals 76 are disposed outward from the leakage channels to retain any leaking coolant.

Figure 4A:
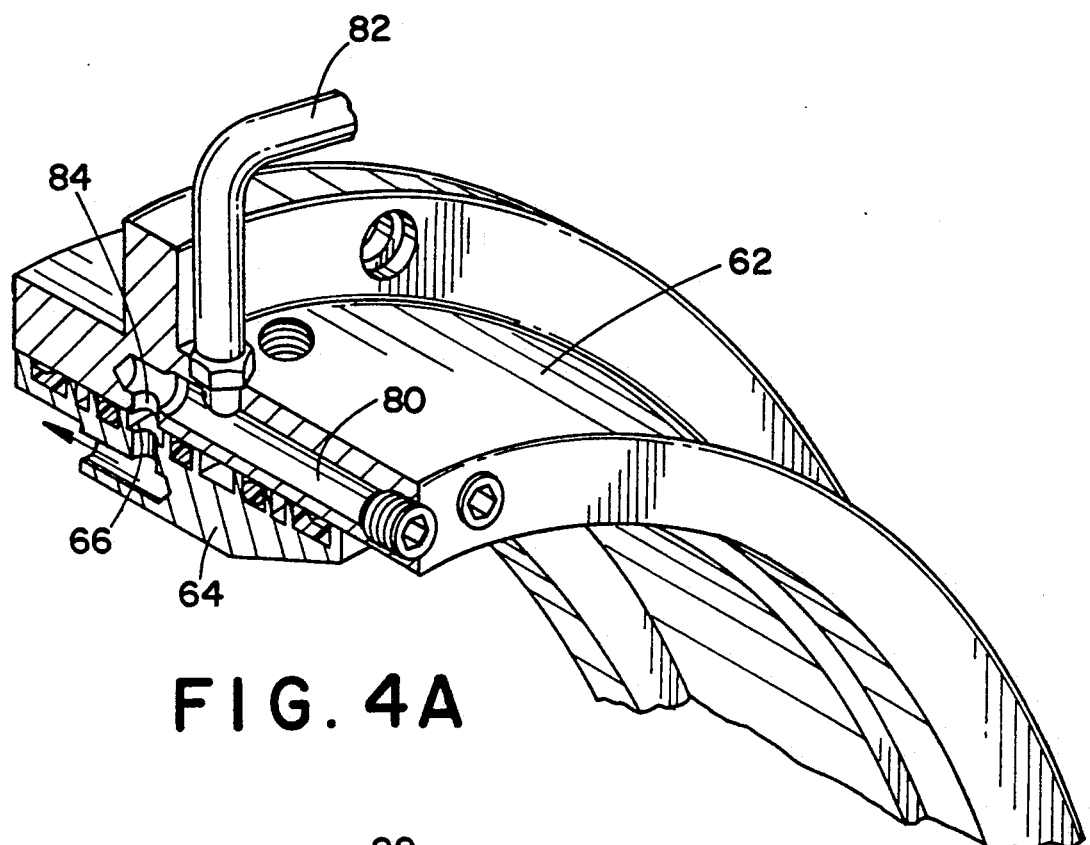
FIGS. 4A, 4B, and 4C are illustrative of the coolant inlet, the coolant return, and the leakage fluid interconnections, respectively, of the fluid slip ring.
Figure 4B:
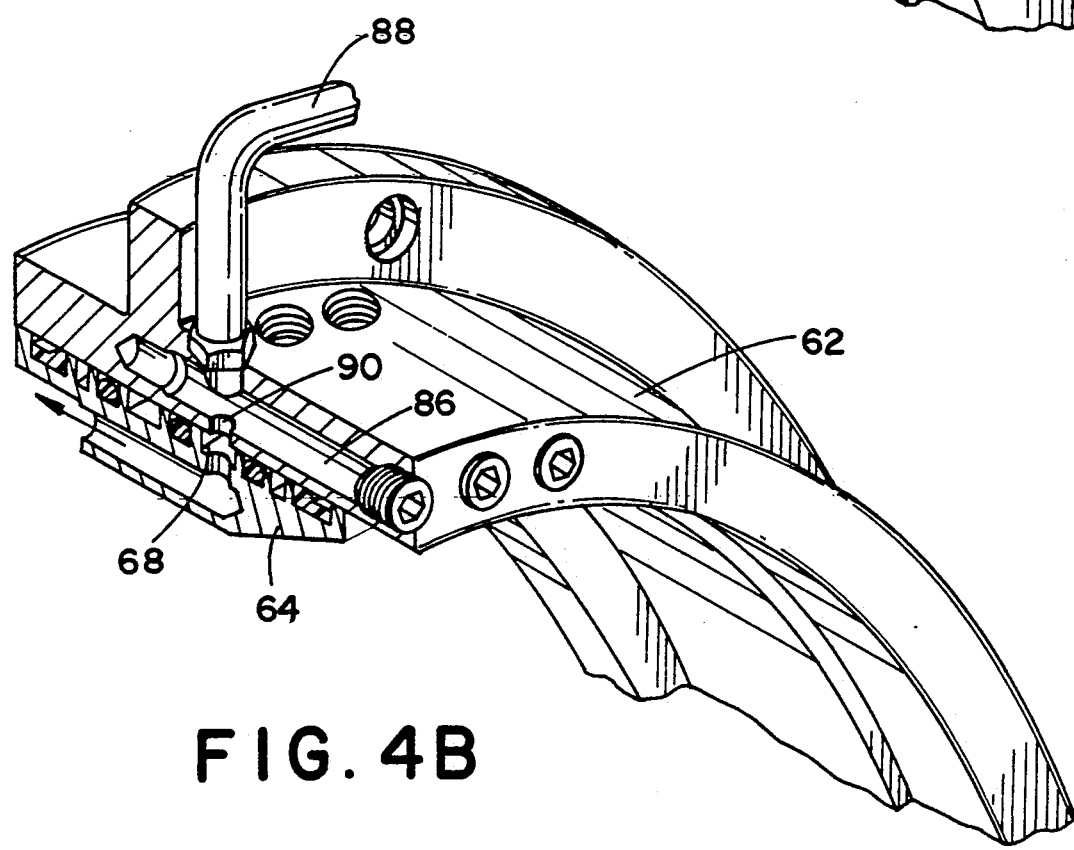
Figure 4C:
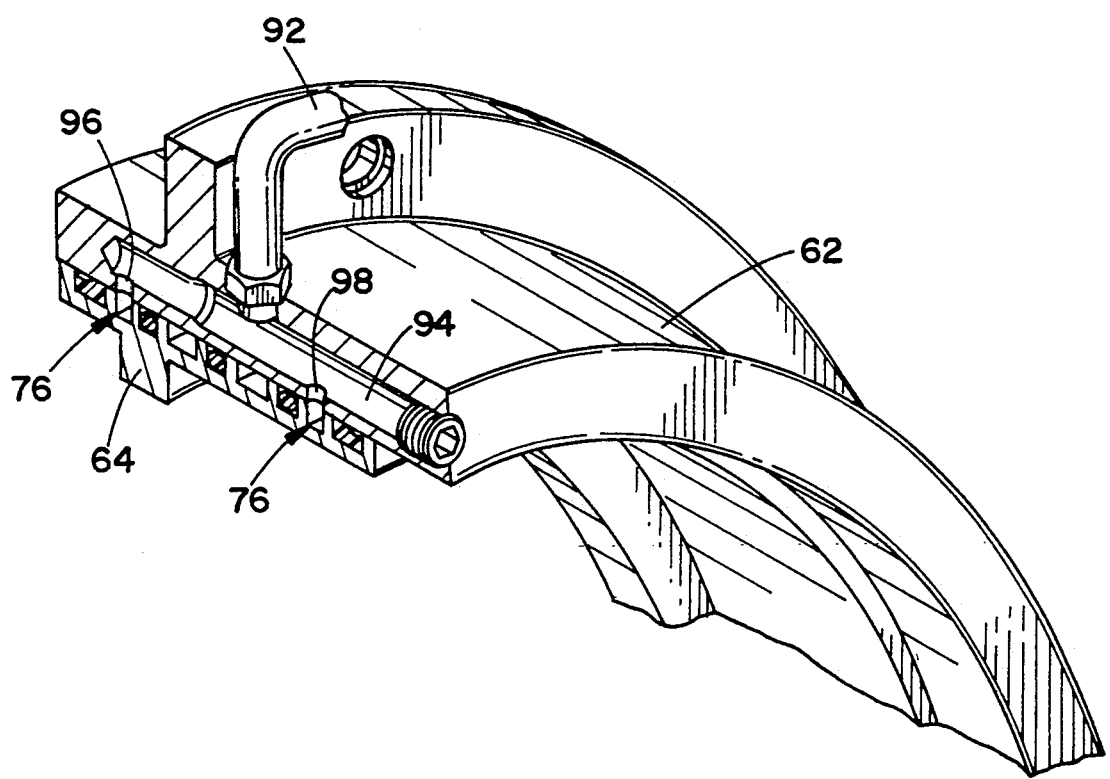

With particular reference to FIGS. 4A, 4B, and 4C, the stationary annular portion 62 has three fluid paths bored therethrough. A first fluid path 80 extends from an inlet connector or coupling 82 to an aperture or port 84 that is in axial alignment with the inlet or chilled cooling fluid channel 66. An outlet passage 86 is defined in fluid communication between an outlet coupling or fitting 88 and an aperture or port 90 that is disposed in longitudinal alignment with the outgoing or hot cooling fluid channel 68. A drain fitting 92 is connected with a leakage fluid passage 94 that has apertures or ports 96, 98 in alignment with the leakage collecting channels 76.

The rotating frame has a chilled fluid path 100 extending from the chilled fluid channel 66 to the heat exchanger 32. Heated fluid is returned from the heat exchanger 32 through path 102 to the hot cooling fluid channel 68.

With reference again to FIG. 1, a circulating means, such as a pump 110, pumps cooled cooling fluid from the chiller D to the inlet channel 66, through the heat exchanger 32 to cool the x-ray tube oil and through the return channel 68 into a reservoir 112. Cooling fluid is drawn from the reservoir, through the chiller and returned by the pump 100 through the fluidic slip ring. The chiller includes a compressor and freon-type refrigerant system for efficiently cooling the cooling fluid. Preferably, the chiller has an air-fluid heat exchanger that discharges heat at the exterior of the building in which the CT scanner is located. Optionally, the oil-coolant heat exchanger 32 may be eliminated and the x-ray tube oil circulated to the chiller.

The invention has been claimed with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment the invention is now claimed to be:

1. A radiographic apparatus comprising:
    a stationary annular slip ring portion and a mating rotating annular slip ring portion, one of the stationary and rotating annular slip ring portions having a series of at least two circumferential channels therein, which channels interact with the other annular portion to form at least first and second fluid carrying passages therebetween;
    a rotatable x-ray tube carrying frame connected with the rotating slip ring portion and connected in fluid communication with the first-end second fluid carrying passages for receiving a cooling fluid cold from the first fluid carrying passage and returning the cooling fluid hot to the second fluid carrying passage;
    a stationary cooling means for cooling the cooling fluid, the cooling means being in fluid communication with the first and second fluid carrying passages for receiving the cooling fluid hot from the second passage and returning the cooling fluid cold to the first passage;
    a fluid circulating means for circulating the cooling fluid through the fluidic slip ring between stationary cooling means and the rotatable frame.

2. The apparatus as set forth in claim 1 wherein the x-ray tube is an oil cooled x-ray tube and further including a heat exchanger mounted to the rotating frame for transferring heat from the x-ray tube cooling oil to the cooling fluid, the heat exchanger being connected with the first and second passages such that the fluid circulating means circulates the cooling fluid cold to the heat exchanger and the cooling fluid hot from the heat exchanger through the second passage to the stationary cooling means.

3. The apparatus as set forth in claim 1 further including a first annular seal disposed between the two channels and additional annular seals disposed longitudinally outward to each of the two channels, such that the seals inhibit fluid from leaving the two channels and from intermixing between the two channels.

4. A radiographic apparatus comprising:
    a rotatable framing carrying a fluid cooled x-ray tube;
    a cooling means for cooling a cooling fluid;
    a fluidic slip ring for providing fluid communication between the cooling means and the x-ray tube carrying frame, the slip ring including:
        matching stationary and rotating rings;
        a series of circumferential channels defined in at least one of the rotating and stationary rings, the channels including at least a hot cooling fluid conveying channel, a cold cooling fluid conveying channel, and a pair of circumferential drain channels disposed to either side of the hot and cold cooling fluid conveying channels for receiving cooling fluid that has leaked therefrom, and,
        sealing means disposed between the hot and cold cooling fluid conveying channels, between the one of the drain channels and the cold cooling fluid conveying channel, between the other drain channel and the hot cooling fluid conveying channel, and outward beyond the drain channels;
    a fluid circulating means for circulating the cooling fluid through the fluidic slip ring between the rotatable frame and the cooling means.

5. The apparatus as set forth in claim 4 wherein the stationary annular ring has a drain passage therethrough and ports in fluid communication with each of the drain channels.

6. The apparatus as set forth in claim 3 wherein the channels are defined in the rotating annular portion and wherein the rotating annular portion includes at least two fluid passages therethrough for carrying cooling fluid to components on the rotating frame.

7. The apparatus as set forth in claim 6 wherein the stationary annular portion has a smooth interior surface that is engaged by the sealing means.

8. The apparatus as set forth in claim 7 further including at least two passages through the stationary annular portion extending between inlet and outlet cooling fluid fittings and apertures disposed in alignment with the channels.

9. A CT scanner comprising:
    a patient receiving region defined within a stationary frame;
    a fluid cooled x-ray tube mounted on a rotating frame for rotation about the patient receiving region, the x-ray tube having an x-ray window through which x-rays are transmitted across the patient receiving region;
    a radiation detection means for detecting radiation which has traversed the patient receiving region;
    an image reconstruction means for reconstructing an image representation from signals generated by the x-ray detection means;
    a fluid slip ring for providing fluid communication between the rotating and stationary frames;
    a cooling fluid circulating means for circulating a cooling fluid through the fluidic slip ring between the stationary and rotating frames.

10. The scanner as set forth in claim 9 wherein the x-ray tube is oil-cooled and further including a heat exchanger for transferring heat from the x-ray tube oil to the cooling fluid, the heat exchanger being mounted on the rotatable frame.

11. A CT scanner comprising:
    a patient receiving region defined within a stationary frame;
    a fluid cooled x-ray tube mounted on a rotating frame for rotation about the patient receiving region, the x-ray tube having an x-ray window through which x-rays are transmitted across the patient receiving region;
    a radiation detection means for detecting radiation which has traversed the patient receiving region;

an image reconstruction means for reconstructing an image representation from signals generated by the x-ray detection means;

a fluid slip ring for providing fluid communication between the rotating and stationary frames, the fluidic slip ring including:
- a rotating annular portion having first and second circumferential cooling fluid channels defined therein;
- a stationary annular portion surrounding the rotatable portion in a generally mating relationship with the channels;
- a sealing means for preventing cooling fluid flow out of the channels between the rotating and stationary annular portions;
- a first fluid passage through the stationary annular portion with a first aperture in alignment with the first channel and a second passage through the stationary annular portion having an aperture in alignment with the second channel;
- a cooling fluid circulating means for circulating a cooling fluid through the fluidic slip ring between the stationary and rotating frames, the stationary annular portion passages being operatively connected with the cooling fluid circulating means, whereby cooling fluid flows through one of the first passages into the first channel, flows from the first channel to the rotating frame, absorbs x-ray tube heat, flows from the rotating frame back to the second channel, and flows through the second stationary annular portion passage.

12. The apparatus as set forth in claim 11 further including a mechanical chiller which is stationarily mounted in fluid communication with the stationary annular portion passages for cooling the cooling fluid.

13. The apparatus as set forth in claim 11 wherein:
- the rotating annular portion further includes a pair of leakage channels disposed longitudinally beyond the first and second channels for receiving cooling fluid which has leaked through the sealing means;
- a leakage sealing means is disposed longitudinally beyond the leakage channels for holding leakage fluid in the leakage channel;
- a third passage is defined through the stationary annular portion and has apertures in alignment with each of the leakage channels for draining cooling fluid therefrom.

14. A CT scanner comprising:
a patient receiving region defined within a stationary frame;
a fluid cooled x-ray tube mounted on a rotating frame for rotation about the patient receiving region, the x-ray tube having an x-ray window through the which x-rays are transmitted across the patient receiving region;
a radiation detection means for detecting radiation which has traversed the patient receiving region;
an image reconstruction means for reconstructing an image representation from signals generated by the x-ray detection means;
a fluid slip ring for providing fluid communication between the rotating and stationary frames, the fluidic slip ring including a stationary annular portion and a rotating annular portion, one of the stationary and rotating annular portions having a series of channels therein, which channels interact with the other annular portion to define at least two fluid carrying paths therebetween;
first ports in the rotating annular portion in fluid communication with the channels for providing a fluid path from one of the channels to the rotating frame and a fluid path from the rotating frame to another of the channels;
a second ports in the stationary annular portion in fluid communication with the channels and the first ports;
a cooling fluid circulating means for circulating a cooling fluid between the stationary and rotating frames, the circulation being from the rotating frame through one of the first ports, one of the channels, and one of the second ports to the stationary frame and from the stationary frame through another of the second ports, another of the channels, and another of the second ports to the stationary frame.

15. The scanner as set forth in claim 14 further including a first annular seal disposed between the two channels and additional annular seals disposed outward to each of the two channels, such that the seals inhibit fluid from leaving the two channels and from intermixing between the two channels.

16. A CT scanner comprising:
a patient receiving region defined within a stationary frame;
a fluid cooled x-ray tube mounted on a rotating frame for rotation about the patient receiving region, the x-ray tube having an x-ray window through which x-rays are transmitted across the patient receiving region;
a radiation detection means for detecting radiation which has traversed the patient receiving region;
an image reconstruction means for reconstructing an image representation from signals generated by the x-ray detection means;
a fluid slip ring for transferring cooling fluid between the rotating and stationary frames, the fluid slip ring includes:
  mating stationary and rotating annular portions,
  first and second cooling fluid channels defined in at least one of the annular portions,
  annular drain channels disposed in at least one of the annular portions on opposite sides of the first and second channels for receiving any cooling fluid that has leaked from the first and second channels and,
  sealing means disposed between the first, second, and drain channels;
a cooling fluid circulating means for circulating a cooling fluid through the first and second channels between the stationary and rotating frames.

17. The scanner as set forth in claim 14 wherein the stationary annular portion has a smooth interior surface that is engaged by the sealing means.

18. A radiographic method comprising:
rotating an x-ray tube around an examination region;
selectively activating the x-ray tube to irradiate at least a portion of the examination region with radiation;
defining first and second annular fluid regions around the examination region;
withdrawing cooling fluid from the first annular regions to cool the x-ray tube and returning heated cooling fluid to the second annular region;
removing the heated cooling fluid from the second annular region;
cooling the removed heated cooling fluid; and,
returning the cooled cooling fluid to the first annular region, whereby the x-ray tube has access to cooling fluid from the first annular region throughout its rotational path around the examination region.

* * * * *